(12) United States Patent
Linley et al.

(10) Patent No.: US 7,711,523 B2
(45) Date of Patent: May 4, 2010

(54) SYSTEM FOR REMOTE MONITORING AND CONTROL OF AN INSTRUMENT

(75) Inventors: Richard Linley, Newtown, CT (US); John A. Olbert, New Fairfield, CT (US)

(73) Assignee: PerkinElmer LAS, Inc., Boston, MA (US)

( * ) Notice: Subject to any disclaimer, the term of this patent is extended or adjusted under 35 U.S.C. 154(b) by 160 days.

(21) Appl. No.: 11/932,380

(22) Filed: Oct. 31, 2007

(65) Prior Publication Data

US 2008/0059124 A1 Mar. 6, 2008

Related U.S. Application Data

(60) Division of application No. 10/855,081, filed on May 27, 2004, now Pat. No. 7,328,135, which is a division of application No. 10/262,084, filed on Sep. 30, 2002, now Pat. No. 6,766,279, which is a continuation of application No. 10/086,914, filed on Mar. 1, 2002, now abandoned.

(60) Provisional application No. 60/272,553, filed on Mar. 1, 2001.

(51) Int. Cl.
*G06F 17/00* (2006.01)
*G06F 19/00* (2006.01)

(52) U.S. Cl. .................. 702/188; 702/183; 702/186; 709/203

(58) Field of Classification Search .............. 702/188, 702/183, 186
See application file for complete search history.

(56) References Cited

U.S. PATENT DOCUMENTS 5,366,896 A * 11/1994 Margrey et al. ............ 436/48

| | | | | |
|---|---|---|---|---|
| 5,521,845 A * | 5/1996 | Ukon et al. .................... 702/33 |
| 5,790,977 A | 8/1998 | Ezekiel ...................... 702/122 |
| 6,049,764 A * | 4/2000 | Stahl ......................... 702/183 |
| 6,085,227 A | 7/2000 | Edlund et al. ............... 709/203 |
| 6,389,464 B1 | 5/2002 | Krishnamurthy et al. .... 709/220 |
| 6,446,192 B1 | 9/2002 | Narasimhan et al. .......... 712/29 |
| 6,490,052 B1 | 12/2002 | Yanagidaira ................ 358/1.15 |
| 6,643,691 B2 * | 11/2003 | Austin ........................ 709/217 |
| 6,658,325 B2 | 12/2003 | Zweig ......................... 700/245 |
| 6,845,401 B1 | 1/2005 | Papadopoulos et al. ..... 709/250 |
| 6,853,867 B1 * | 2/2005 | Klindt et al. .................. 700/83 |
| 6,871,211 B2 | 3/2005 | Labounty et al. ............ 709/203 |
| 6,932,611 B2 | 8/2005 | Shen et al. ................... 434/276 |
| 2001/0029521 A1 | 10/2001 | Matsuda et al. ............. 709/201 |
| 2002/0002611 A1 | 1/2002 | Vange ......................... 709/223 |
| 2002/0065898 A1 | 5/2002 | Leontiev et al. ............. 709/208 |
| 2002/0099818 A1 | 7/2002 | Russell et al. ............... 709/224 |
| 2002/0173877 A1 | 11/2002 | Zweig ......................... 700/245 |
| 2003/0135587 A1 | 7/2003 | Fisher et al. ................. 709/219 |
| 2006/0200253 A1* | 9/2006 | Hoffberg et al. .............. 700/19 |

* cited by examiner

*Primary Examiner*—Hal D Wachsman
(74) *Attorney, Agent, or Firm*—St.Onge Steward Johnston & Reens LLC

(57) ABSTRACT

The invention relates to a web-based instrument and data management system and method including software executing on an instrument controller computer system that receives a web file from a web browsing software executing on a remote computer. The web-based interface also extracts a user identifier and a requested action, determines with the user is authorized for the requested action and performs the action is the user is authorized. If not the web-based interface generates and transmits a web file indicating that the user is not authorized for the requested action.

14 Claims, 7 Drawing Sheets

SYSTEM FOR REMOTE MONITORING AND CONTROL OF AN INSTRUMENT

CROSS-REFERENCE TO RELATED APPLICATIONS

This is a divisional patent application of U.S. patent application Ser. No. 10/855,081, filed May 27, 2004, which is a divisional application of U.S. patent application Ser. No. 10/262,084, filed Sep. 30, 2002, now U.S. Pat. No. 6,766,279, which is a continuation of U.S. patent application Ser. No. 10/086,914, filed Mar. 1, 2002, now abandoned which in turn claims the benefit under 35 U.S.C. 119(e) of U.S. Provisional Patent Application No. 60/272,553, filed Mar. 1, 2001.

FIELD OF THE INVENTION

The present invention relates to an improved analytical instrument, and more particularly to an analytical instrument incorporating remote monitoring and control features.

BACKGROUND OF THE INVENTION

Numerous types of analytical instruments are well known and widely used in many settings. Common examples of such instruments include molecular spectroscopy instruments, thermal and elemental analysis instruments, inorganic analysis instruments, chromatography instruments, and numerous others. Such instruments can often be found in research laboratories, universities, medical laboratories, and in many other locations.

Traditionally, analytical instruments included some integrated type of user interface which allowed a user to control operation of the instrument and to observe instrument output. However, this arrangement suffered from a number of disadvantages. One such disadvantage was that the interface, being an integral part of the instrument, was not easily modified or upgradeable. If it was desired to upgrade the interface in any significant way, it was often necessary to replace the entire interface. Another disadvantage was that, although the integrated interfaces may have allowed for some rudimentary storage and manipulation of output data, such functions were typically severely limited.

With the advent of the personal computer, these disadvantages were obviated by interfacing analytical instruments with an instrument controller computer rather than or in addition to the integrated interface. The user interface could then comprise computer software executing on the instrument controller computer. This allowed for the provision of more complex instrument operations as well as facilitating the storage and manipulation of output data. Connecting the instrument to an instrument control computer having instrument interface software executing thereon also provided the benefit of allowing the instrument control interface to be easily modified or updated simply by updating the software. However, such arrangements still suffered from a number of disadvantages. One of such disadvantages was that the instrument could only be controlled by, and the instrument output data could only by viewed on, the particular instrument control computer directly connected to the instrument.

It was discovered that this and other disadvantages could be obviated if the instrument controller computer was connected to a network of computers. Referring to FIG. 1, a known network 10 incorporating an instrument controller computer 12 is shown. Instrument controller computer 12 generally comprises a CPU, a memory, and various input and output devices, as is commonly known. One or more analytical instruments 14, 16, 18 are directly connected to instrument controller computer 12 by way of some hard-wired connection, such as a serial or parallel connection. Executing on instrument controller computer 12 is instrument interface software. The instrument interface software is used to control each of analytical instruments 14, 16, 18 connected to instrument controller computer 12. More specifically, instrument interface software receives user input, for example, by receiving commands via keystrokes, menus, icons, etc., and translates this user input into control signals which are transmitted to the appropriate one of analytical instruments 14, 16, 18 by way of the hard-wired connection. The instrument interface software also receives signals output by each of analytical instruments 14, 16, 18 via the hard-wired connection, translates the signals into data useful to the user, and displays the data. The data may also be stored on an instrument database 20 connected to instrument controller computer 12.

It should be noted that the instrument interface software is typically unique to each instrument 14, 16, 18 being controlled. Thus, different software must be employed to control different types or even different models of instruments supplied by the same manufacturer and to control the same types of instruments supplied by different manufacturers. As such, the particular instrument cannot be controlled by instrument controller computer 12 unless the unique instrument interface software which is appropriate for the particular instrument desired to be controlled has been installed on instrument controller computer 12.

One or more additional computers 22, 24, 26 may be in communication with instrument controller computer 12 by a network connection 28, such as an intranet, a local area network (LAN), a wide area network (WAN), a virtual private network (VPN) or the like. Computers 22, 24, 26 may be used to control one or more of instruments 14, 16, 18 so long as computer 22, 24, 26 has the unique instrument interface software which is appropriate for the particular instrument desired to be controlled installed thereon. When such is the case, instruments 14, 16, 18 are controlled by computers 22, 24, 26 as described above with respect to instrument controller computer 12. More specifically, the instrument interface software executing on computers 22, 24, 26 receives commands via keystrokes, menus, icons, etc., and translates this user input into control signals which are transmitted to the appropriate one of analytical instruments 14, 16, 18 via network connection 28, instrument controller computer 12 and the hard-wired connection. The instrument interface software also receives signals output by each of analytical instruments 14, 16, 18 via the hard-wired connection, instrument controller computer 12 and network connection 28, translates the signals into data useful to the user, and displays the data.

Although network 10 allows a user to control instruments 14, 16, 18 using computers 22, 24, 26 other than instrument controller computer 12 directly connected to instruments 14, 16, 18, network 10 still suffers from a number of disadvantages. One such disadvantage is that any of computers 22, 24, 26 which are utilized to control instruments 14, 16, 18 must have the appropriate instrument interface software installed thereon. This is disadvantageous for a number of reasons. For example, it may be desirable for a user to be able to control an instrument from a computer which is not typically used for instrument control (e.g., from home or while traveling). It would be highly disadvantageous to require the user to install the appropriate instrument interface software on such computers. Moreover, when the instrument interface software is updated, network 10 would require that the instrument interface software be updated on each of the (possibly numerous)

computers 22, 24, 26 on network 10 in addition to instrument controller computer 12. This would be a time-consuming and inefficient process.

What is desired, therefore, is an analytic instrument which incorporates remote monitoring and control features, which includes an interface which is easily modifiable or upgradeable, which facilitates storage and manipulation of output data, and which does not require that instrument interface software unique to the instrument be installed on computers used to remotely monitor and control the instrument.

SUMMARY OF THE INVENTION

Accordingly, it is an object of the present invention to provide an analytic instrument which incorporates remote monitoring and control features.

Another object of the present invention is to provide an analytic instrument having the above characteristics and which includes an interface which is easily modifiable or upgradeable.

A further object of the present invention is to provide an analytic instrument having the above characteristics and which facilitates storage and manipulation of output data.

Still another object of the present invention is to provide an analytic instrument having the above characteristics and which does not require that instrument interface software unique to the instrument be installed on computers used to remotely monitor and control the instrument.

In one embodiment, these and other objects of the present invention are achieved by provision of a web-based instrument and data management system including an instrument controller computer system having at least one analytical instrument connected thereto. At least one remote computer is in communication with the instrument controller computer system via a network connection, the at least one remote computer having web browser software executing thereon. Web-based instrument interface software executing on the instrument controller computer system receives a web file from the web browsing software executing on the at least one remote computer, extracts a command or a request for status information from the web file, generates and transmits to the at least one analytical instrument a signal indicative of the extracted command or request for status information, receives a signal from the at least one analytical instrument indicative of the status thereof, and generates and transmits to the web browsing software executing on the at least one remote computer a web file based upon the received signal from the at least one analytical instrument indicative of the status thereof.

In a related embodiment, the system further includes an instrument database accessible by the instrument controller computer system. In this embodiment, web-based instrument interface software executing on the instrument controller computer system receives a web file from the web browsing software executing on the at least one remote computer, extracts a request for data from the web file, retrieves the requested data from the at least one analytical instrument or the instrument database, and generates and transmits to the web browsing software executing on the at least one remote computer a web file based upon the retrieved requested data.

The instrument controller computer system may comprise a single instrument controller computer or an instrument controller computer and a web server computer. Moreover, the at least one remote computer may be in communication with the instrument controller computer system via the Internet. Preferably, the web files comprise HTML files. It is also preferable that the web-based instrument interface software confirms whether a user of the at least one remote computer is authorized for the command, the request for status information or the request for data before executing the user's command.

In another aspect of the invention, a web-based instrument and data management system includes an instrument controller computer system having at least one analytical instrument connected thereto. The system also includes a permissions database accessible by the instrument controller computer system. At least one remote computer is in communication with the instrument controller computer system via a network connection, the at least one remote computer having web browser software executing thereon. Web-based instrument interface software executing on the instrument controller computer system receives a web file from the web browsing software executing on the at least one remote computer, extracts a user identifier and a requested action from the web file, determines whether a user of the at least one remote computer is authorized for the requested action based upon the user identifier, the requested action and data stored on the permissions database, performs the requested action if the user is authorized, and if the user is not authorized generates and transmits to the web browsing software executing on the at least one remote computer a web file indicating that the user is not authorized for the requested action.

The requested action may comprise an instrument command, a request for instrument status information or a request for data.

The invention and its particular features and advantages will become more apparent from the following detailed description considered with reference to the accompanying drawings.

DETAILED DESCRIPTION OF THE INVENTION

Figure 2:
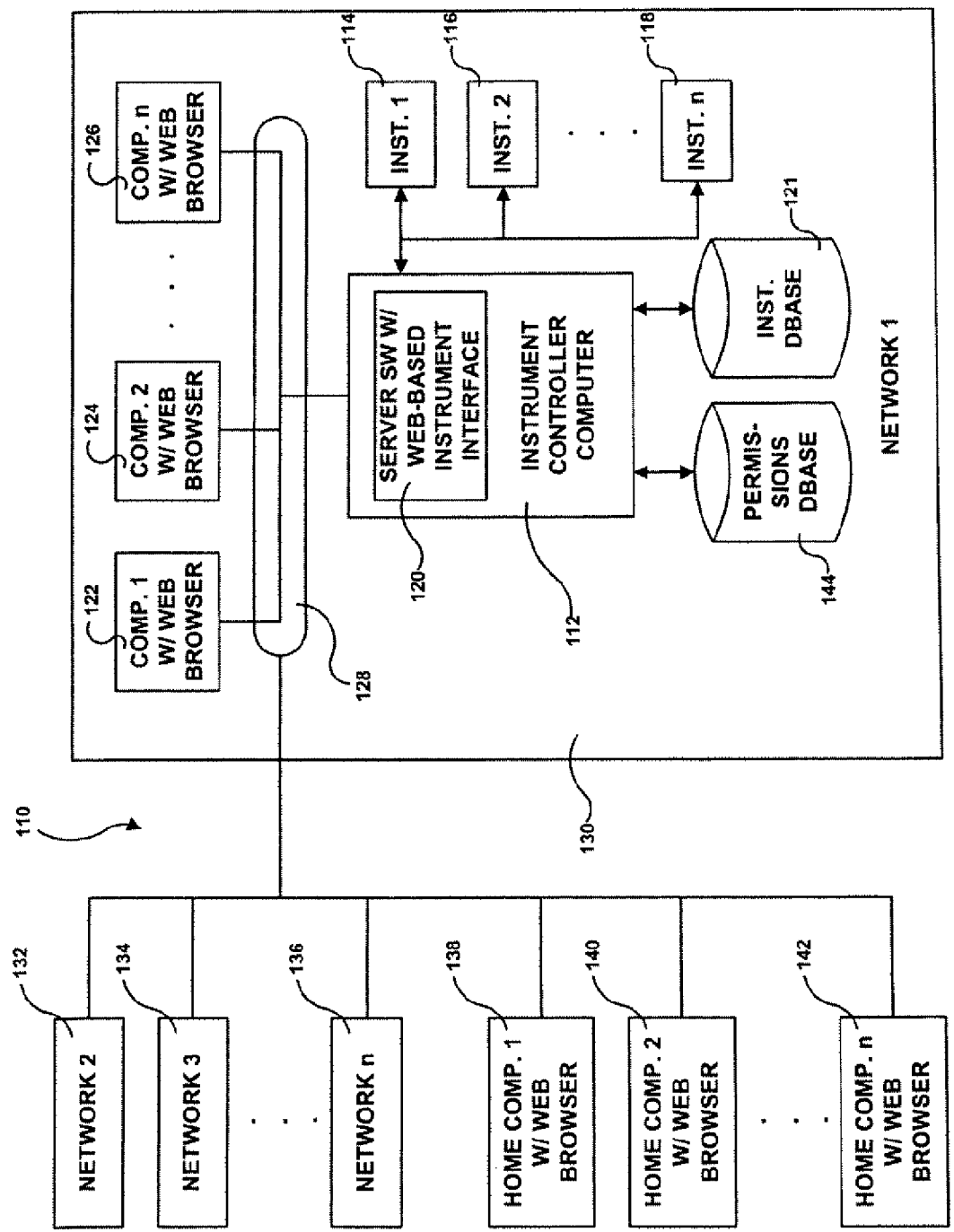
FIG. 2 is a block diagram of an embodiment of an analytical instrument incorporating a web-based instrument and data management system in accordance with the present invention.

Referring now to FIG. 2, a web-based instrument and data management system 110 in accordance with the present invention is shown. System 110 includes an instrument controller computer 112 which generally comprises a CPU, a memory, and various input and output devices, as is commonly known. One or more analytical instruments 114, 116, 118 are directly connected to instrument controller computer 112 by way of some hardwired connection, such as a serial or parallel connection. Executing on instrument controller computer 112 is web-based instrument interface software 120. One or more additional computers 122, 124, 126 may be in communication with instrument controller computer 112 by a network connection 128, such as an intranet, a local area network (LAN), a wide area network (WAN), a virtual private network (VPN) or the like. Instrument controller computer 112 and additional computers 122, 124, 126 thus comprise a first network 130 connected by network connection 128.

Figure 1:
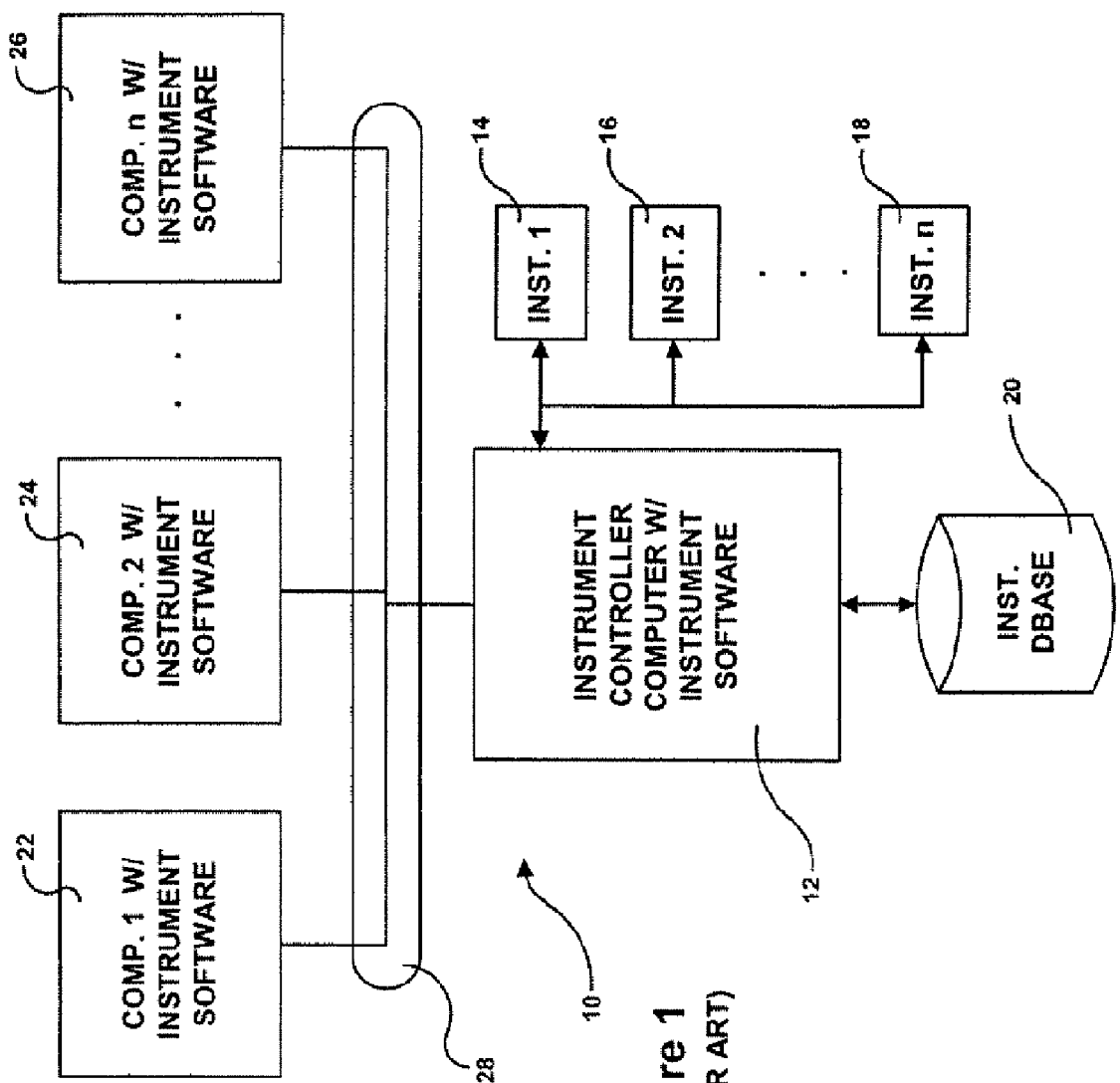
FIG. 1 is a block diagram of an analytical instrument incorporating a prior art instrument controller network.

As is similar to network 10 shown in FIG. 1, web-based instrument interface software 120 is used to control each of analytical instruments 114, 116, 118 connected to instrument controller computer 112. More specifically, web-based instrument interface software 120 receives user input, for example, by receiving commands via keystrokes, menus, icons, etc., and translates this user input into control signals which are transmitted to the appropriate one of analytical instruments 114, 116, 118 by way of the hard-wired connection. Web-based instrument interface software 120 also receives signals output by each of analytical instruments 114, 116, 118 via the hard-wired connection, translates the signals into data useful to the user, and displays the data. The data may also be stored on an instrument database 121 connected to instrument controller computer 112.

However, unlike network 10 shown in FIG. 1, web-based instrument interface software 120 is web-enabled, meaning that it may be implemented on a system of the type illustrated in FIG. 2 which is comprised of a client side (comprising additional computers 122, 124, 126) and server side (comprising instrument controller computer 112) interconnected by network connection 128. On the client side of the system, each of computers 122, 124, 126 runs a web browser. Computer 122, 124, 126 may be any suitable type of computer such as an Apple computer, IBM or IBM compatible computer, UNIX workstation, etc. On the server side of the system, instrument controller computer 112 has web server software running on an appropriate machine as is known in the art. The web server software may comprise a part of instrument interface software 120 or may be discrete therefrom. The web server software may comprise, for example, Microsoft Information Server web server software or Peer Web Service web server software including the Active Server Pages framework incorporating a scripting engine.

The client side of the system may also comprise additional computers on additional networks 132, 134, 136 as well as additional stand alone computers, such as home computers 138, 140, 142, connected to instrument controller computer 112 via the Internet. All that is required of additional computers on additional networks 132, 134, 136 and additional stand alone computers, such as home computers 138, 140, 142, is that each of such computers has a web browser running thereon. In addition, instrument and data management system 110 may include a permissions database 144 accessible by instrument controller computer 112, the purpose of which is described more fully below.

Figure 3:
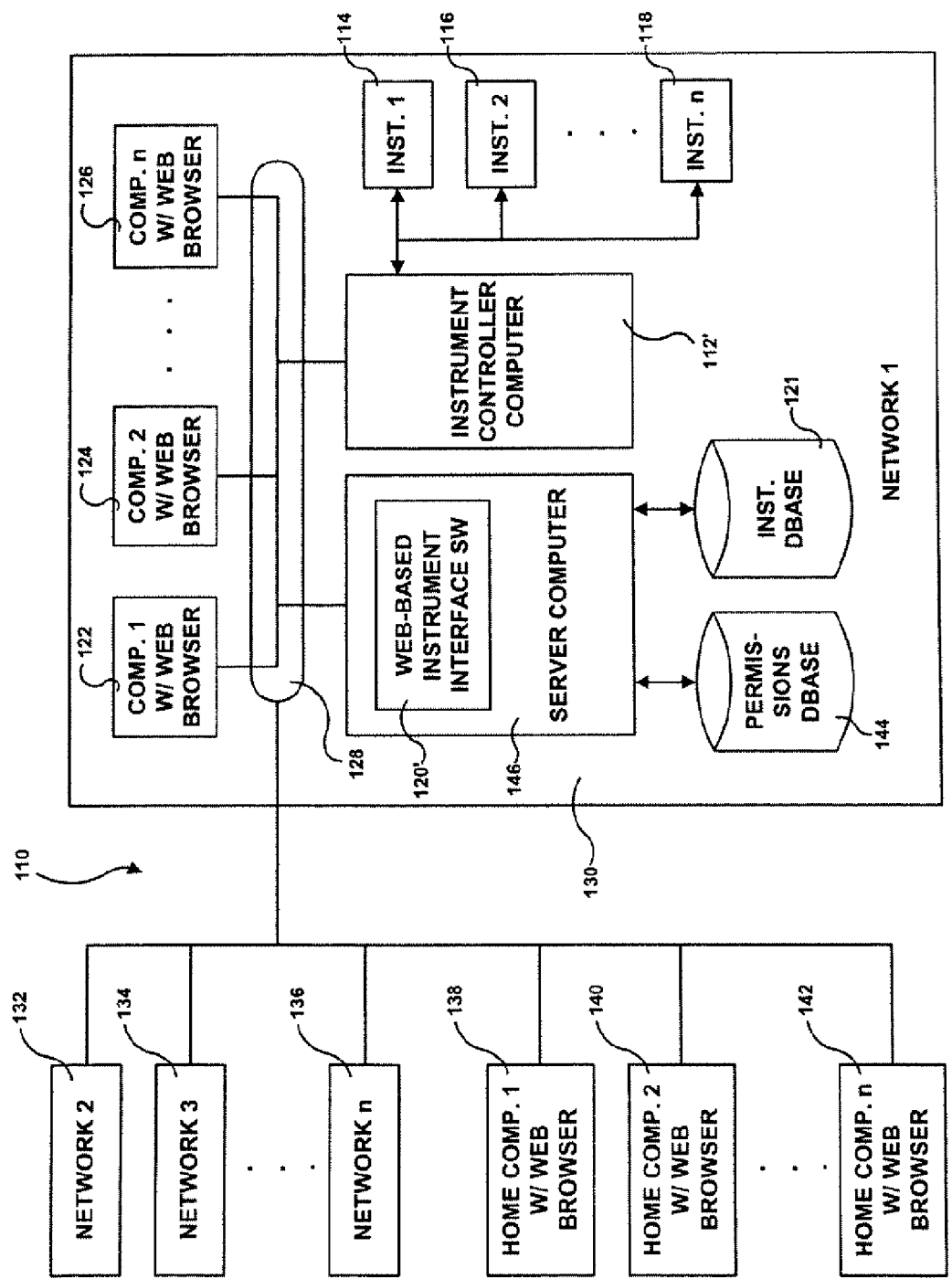
FIG. 3 is a block diagram of another embodiment of an analytical instrument incorporating a web-based instrument and data management system in accordance with the present invention.

In another embodiment, shown in FIG. 3, the server software of system 110' is running on a server computer 146, rather than on instrument controller computer 112'. In this case, web-based instrument interface software 120' may also be running on server computer 146. In substantially all other respects, instrument and data management system 110' operates as discussed with respect to instrument and data management system 110.

Figure 4:
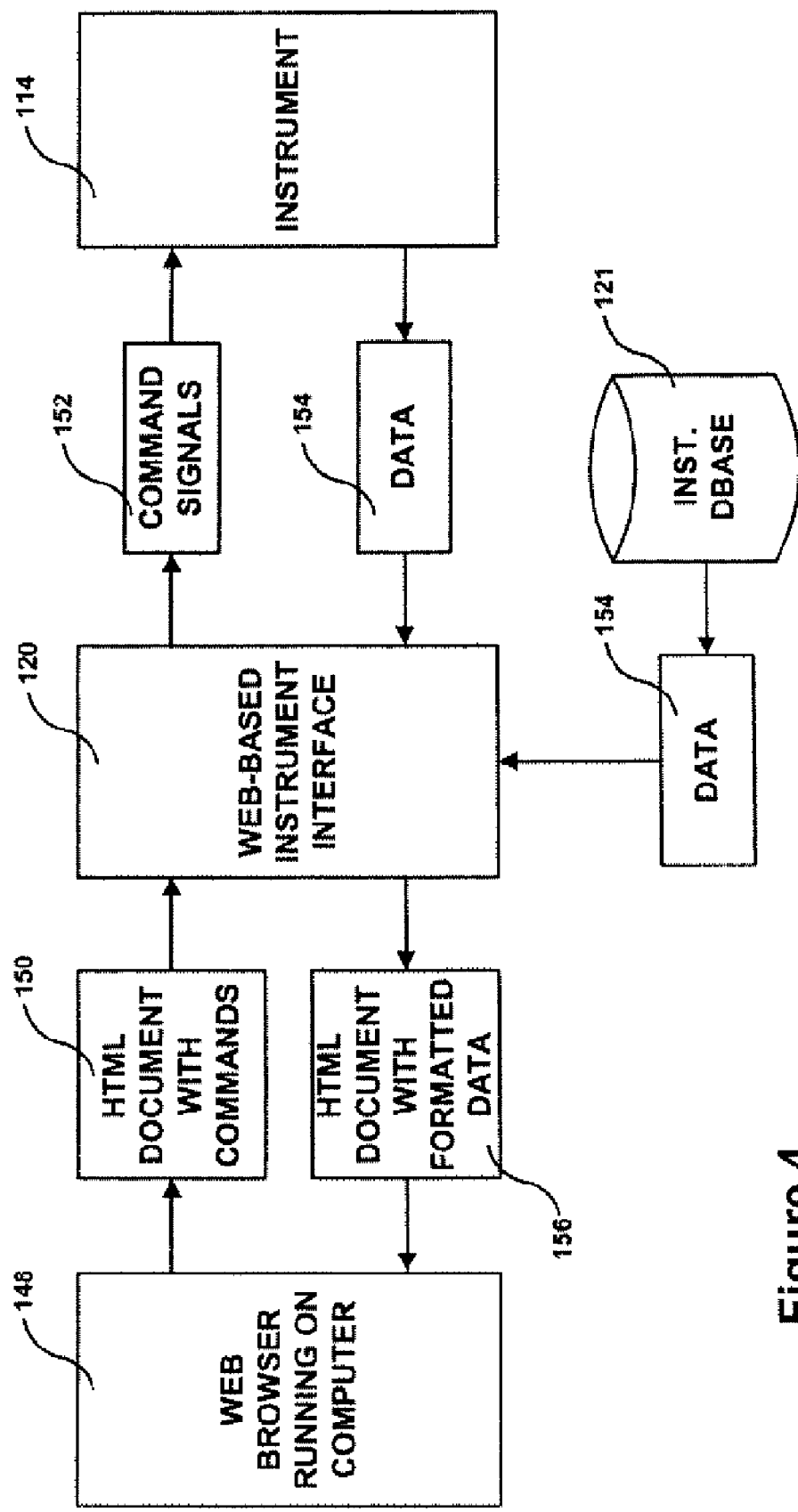
FIG. 4 is a flow chart illustrating in more detail operation of the analytical instrument incorporating a web-based instrument and data management system of FIGS. 2 and 3.

In one embodiment, shown in FIG. 4, web-based instrument interface 120 generates HTML files using Active Server Page files in response to requests from the web browser 148 running on computers on the client side (including computers 122, 124, 126, additional computers on additional networks 132, 134, 136 and additional stand alone computers, such as home computers 138, 140, 142). More specifically, web-based instrument interface 120 receives input, including commands, from remote users via an HTML file 150 via a network connection. Web-based instrument interface 120 extracts commands from HTML file 150 and generates and transmits command signals 152 to an instrument, for example instrument 114. Instrument 114 can then execute the commands represented by command signals 152. Remote users can view and manage data 154 received either directly from instrument 114 or from instrument database 121 in a similar manner. Data 154 is received by web-based instrument interface 120, and is incorporated into an HTML file 156 which is then transmitted to web browser 148 via a network connection. In this manner instrument 114 can be controlled and monitored from a remote location using a computer with only a web browser running thereon.

Figure 5:
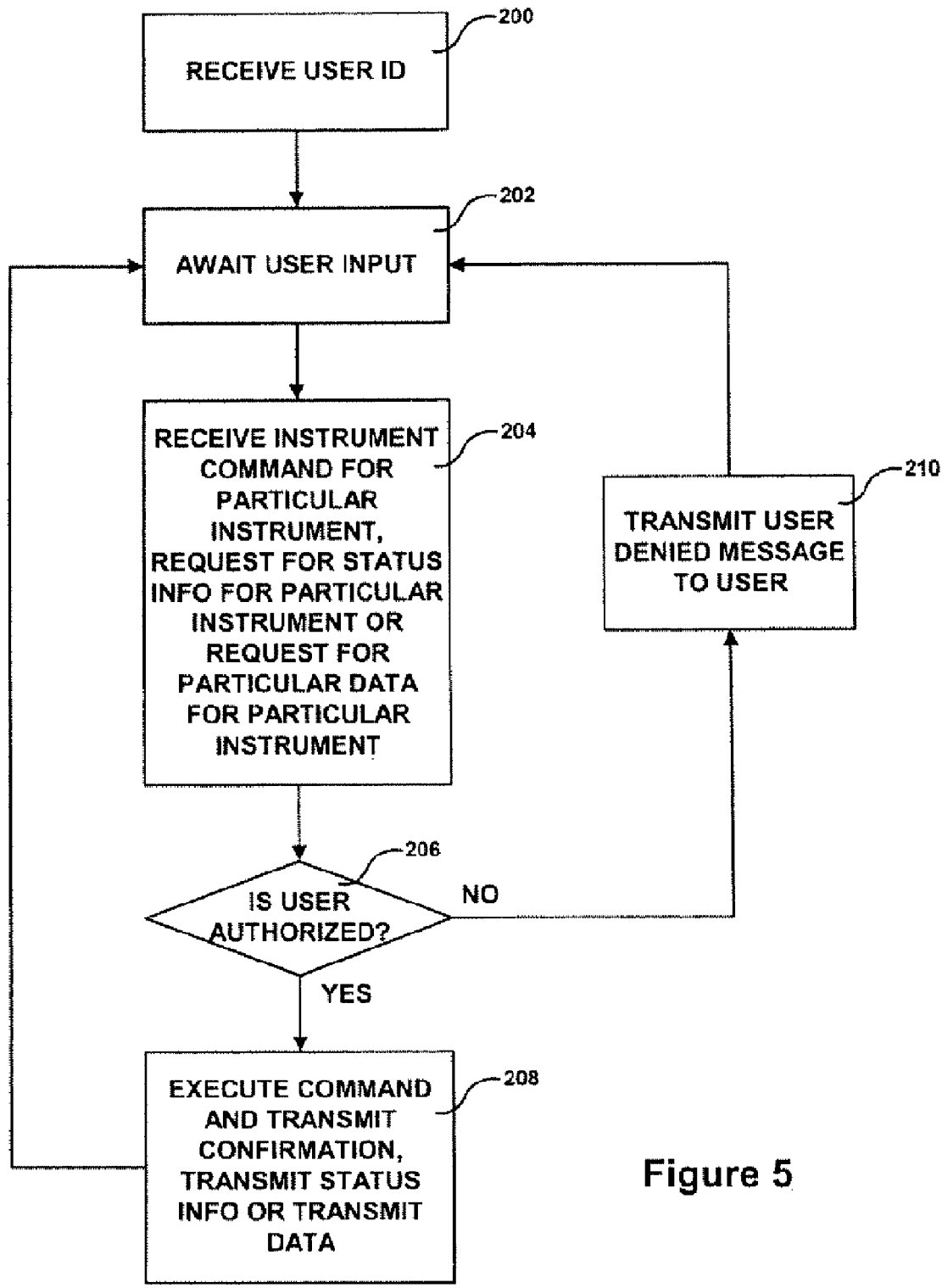
FIG. 5 is a flow chart illustrating in more detail operation of an embodiment of an authorization scheme which may be employed by the analytical instrument incorporating a web-based instrument and data management system of FIGS. 2 and 3.

Web-based instrument interface 120 preferably includes a user authorization routine to prevent unauthorized control of instruments and/or access to unauthorized data. Referring now to FIG. 5, an example of such an authorization scheme is illustrated. Web-based instrument interface 120 receives from the user a unique user identifier at 200, and awaits user input at 202. At 204, web-based instrument interface 120 receives from the user an instrument command for a particular one of instruments 114, 116, 118, a request for status information data for a particular one of instruments 114, 116, 118, and/or a request for particular data for a particular one of instruments 114, 116, 118. Web-based instrument interface 120 then determines, at 206, whether the particular user (based upon the received user identifier) is authorized for the requested action. The information to allow web-based instrument interface to make this determination is stored on permissions database 144. If the user is so authorized, web-based instrument interface 120 executes the requested command and/or transmits the requested status information or data, as indicated at 208. If the user is not so authorized, web-based instrument interface 120 generates and transmits to the user a message, as indicated at 210, informing the user that he or she is not authorized for the requested action. Web-based instrument interface 120 then awaits further user input.

Figure 6:
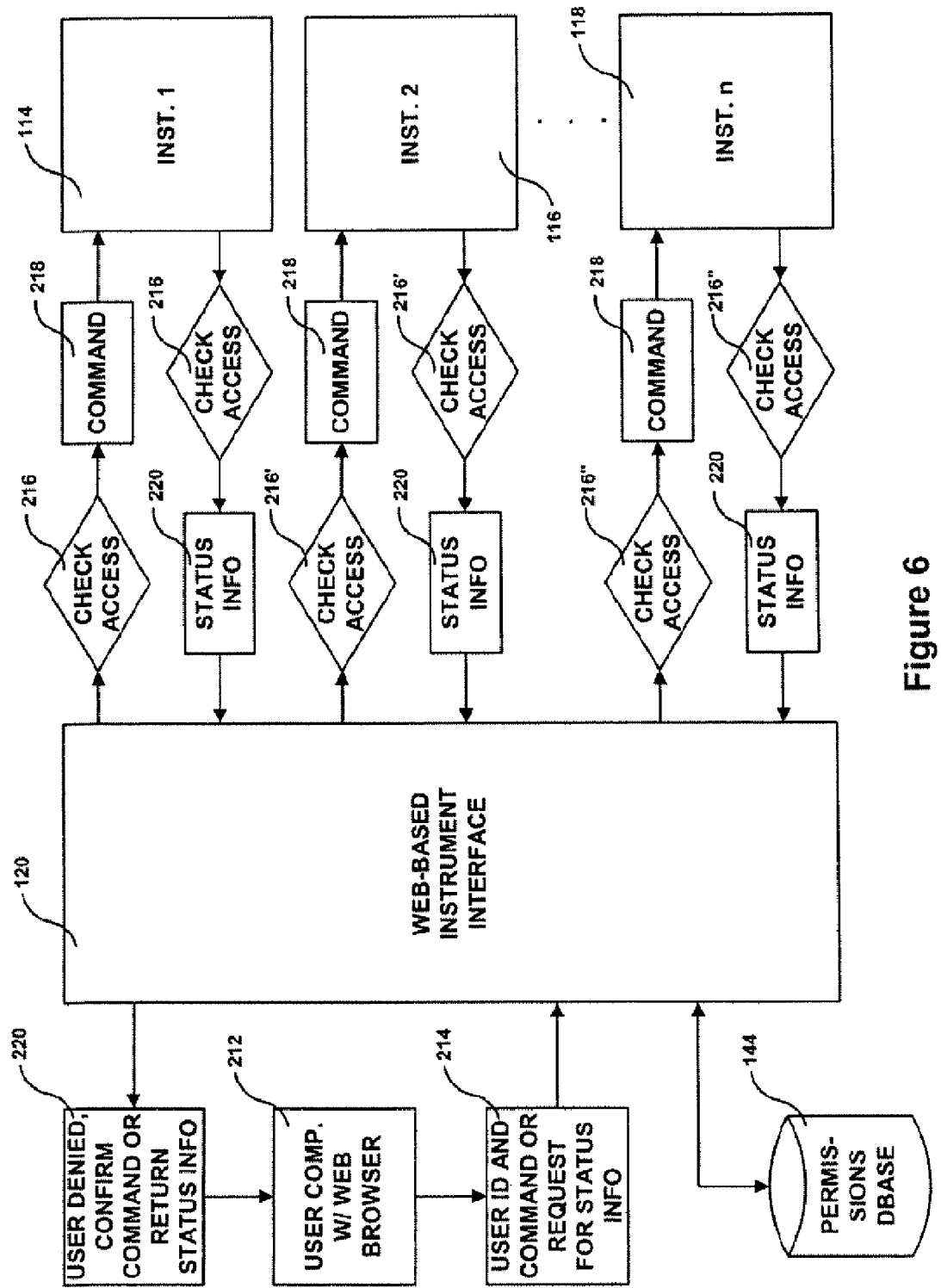
FIG. 6 is a flow chart illustrating in more detail the instrument control and status monitoring aspects of the analytical instrument incorporating a web-based instrument and data management system of FIGS. 2 and 3.

Referring now to FIG. 6, the command and status information portion of the authorization scheme is shown in more detail. A user, by way of a user computer 212 running a web browser transmits to web-based instrument interface 120 one or more HTML files 214 which include his or her unique user identifier and an instrument command for a particular one of instruments 114, 116, 118 and/or a request for status information data for a particular one of instruments 114, 116, 118. Web-based instrument interface 120 then determines for the particular one of instruments 114, 116, 118 for which action was requested (as indicated at 216, 216', 216") whether the user is authorized for the requested action. If the user is so authorized, the command is transmitted by web-based instrument interface 120 to the appropriate instrument 114, 116, 118 (as indicated at 218) and/or the status information is transmitted by the appropriate instrument 114, 116, 118 to web-based instrument interface 120 (as indicated at 220).

Web-based instrument interface 120 then generates and transmits to user computer 212 an HTML file 220 informing the user that he or she is not authorized for the requested action, confirming that the requested command has been executed or displaying the requested instrument status information.

Data concerning whether the user is authorized for the requested action is stored on permissions database 144 which is accessible by web-based instrument interface. It should be understood that great flexibility is possible using this authorization scheme. For example, as illustrated in FIG. 6, the user may be authorized to give commands and receive status information for only one or a select number of instruments 114, 116, 118. Moreover, the user may be authorized, for example, to view status information for one or more instruments 114, 116, 118, but not be authorized to give commands. Furthermore, the user may be authorized only to give certain commands and/or to view only certain status information for particular instruments 114, 116, 118.

Figure 7:
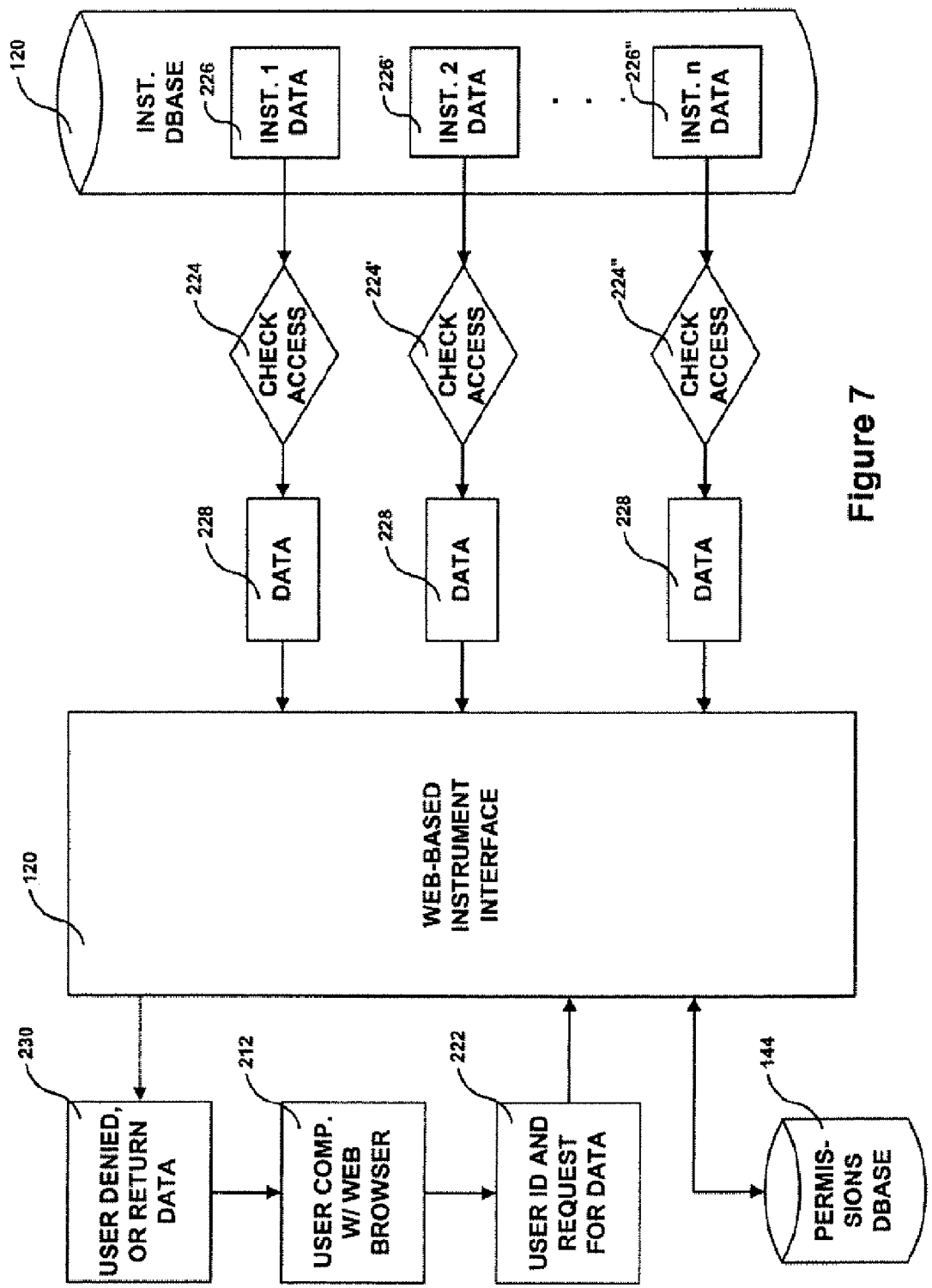
FIG. 7 is a flow chart illustrating in more detail the data management aspect of the analytical instrument incorporating a web-based instrument and data management system of FIGS. 2 and 3.

Referring now to FIG. 7, the data management portion of the authorization scheme is shown in more detail. A user, by way of a user computer 212 running a web browser transmits to web-based instrument interface 120 one or more HTML files 222 which include his or her unique user identifier and a request for data for a particular one of instruments 114, 116, 118. Web-based instrument interface 120 then determines for the particular one of instruments 114, 116, 118 for which data was requested (as indicated at 224, 224',224") whether the user is authorized to view the requested data. If the user is so authorized, the data 226, 226', 226" is transmitted by the instrument database 120 to web-based instrument interface 120 (as indicated at 228). Web-based instrument interface 120 then generates and transmits to user computer 212 an HTML file 230 informing the user that he or she is not authorized to view the requested data or displaying the requested data.

Data concerning whether the user is authorized for the requested action is stored on permissions database 144 which is accessible by web-based instrument interface. It should be understood that great flexibility is possible using this authorization scheme. For example, as illustrated in FIG. 7, the user may be authorized to view data for only one or a select number of instruments 114, 116, 118. Moreover, the user may be authorized only to view certain data files for a particular instrument, but not other data files for that instrument.

The present invention, therefore, provides an analytic instrument which incorporates remote monitoring and control features, which includes, an interface which is easily modifiable or upgradeable, which facilitates storage and manipulation of output data, and which does not require that instrument interface software unique to the instrument be installed on computers used to remotely monitor and control the instrument.

Although the invention has been described with reference to a particular arrangement of parts, features and the like, these are not intended to exhaust all possible arrangements or features, and indeed many other modifications and variations will be ascertainable to those of skill in the art.

What is claimed is:

1. A web-based instrument and data management system comprising:
    an instrument controller computer system;
    at least one analytical instrument connected to said instrument controller computer system;
    a permissions database accessible by said instrument controller computer system;
    at least one remote computer in communication with said instrument controller computer system via a network connection, said at least one remote computer having web browser software executing thereon; and
    web-based instrument interface software executing on said instrument controller computer system, said web-based instrument interface software receiving a web file from the web browsing software executing on said at least one remote computer, extracting a user identifier and a requested action from the web file, determining whether a user of said at least one remote computer is authorized for the requested action based upon the user identifier, the requested action and data stored on said permissions data-base, performing the requested action if the user is authorized, and if the user is not authorized generating and transmitting to the web browsing software executing on said at least one remote computer a web file indicating that the user is not authorized for the requested action.

2. The web-based instrument and data management system of claim 1 wherein said instrument controller computer system comprises a single instrument controller computer.

3. The web-based instrument and data management system of claim 1 wherein said instrument controller computer system comprises an instrument controller computer and a web server computer.

4. The web-based instrument and data management system of claim 1 wherein said at least one remote computer is in communication with said instrument controller computer system via the Internet.

5. The web-based instrument and data management system of claim 1 wherein the web files comprise HTML files.

6. The web-based instrument and data management system of claim 1 wherein the requested action comprises an instrument command.

7. The web-based instrument and data management system of claim 1 wherein the requested action comprises a request for instrument status.

8. The web-based instrument and data management system of claim 1 wherein the requested action comprises a request for data.

9. A method of web-based instrument and data management comprising the steps of:
    providing an instrument controller computer system having at least one analytical instrument connected thereto;
    providing a permissions database accessible by the instrument controller computer system;
    providing at least one remote computer in communication with the instrument controller computer system via a network connection, the at least one remote computer having web browser software executing thereon;
    receiving a web file from the web browsing software executing on the at least one remote computer;
    extracting a user identifier and a requested action from the web file;
    determining whether a user of the at least one remote computer is authorized for the requested action based upon the user identifier, the requested action and data stored on the permissions database;
    performing the requested action if the user is authorized; and
    generating and transmitting to the web browsing software executing on the at least one remote computer, if the user is not authorized, a web file indicating that the user is not authorized for the requested action.

10. The method of web-based instrument and data management of claim 9 wherein the at least one remote computer is in communication with the instrument controller computer system via the Internet.

11. The method of web-based instrument and data management of claim 9 wherein the web files comprise HTML files.

12. The method of web-based instrument and data management of claim 9 wherein the requested action comprises an instrument command.

13. The method of web-based instrument and data management of claim 9 wherein the requested action comprises a request for instrument status.

14. The method of web-based instrument and data management of claim 9 wherein the requested action comprises a request for data.

* * * * *